(12) United States Patent
Machida et al.

(10) Patent No.: US 8,951,395 B2
(45) Date of Patent: Feb. 10, 2015

(54) BIOSENSOR

(75) Inventors: Reiko Machida, Takasaki (JP); Takao Yokoyama, Takasaki (JP); Yayoi Irie, Takasaki (JP); Hisako Takagi, Takasaki (JP); Yoshihiko Umegae, Takasaki (JP); Toshio Tanabe, Takasaki (JP)

(73) Assignee: Nippon Kayaku Kabushiki Kaisha (JP)

( * ) Notice: Subject to any disclaimer, the term of this patent is extended or adjusted under 35 U.S.C. 154(b) by 163 days.

(21) Appl. No.: 12/741,242

(22) PCT Filed: Nov. 5, 2008

(86) PCT No.: PCT/JP2008/070095
§ 371 (c)(1),
(2), (4) Date: Aug. 9, 2010

(87) PCT Pub. No.: WO2009/060849
PCT Pub. Date: May 14, 2009

(65) Prior Publication Data
US 2011/0031118 A1 Feb. 10, 2011

(30) Foreign Application Priority Data
Nov. 5, 2007 (JP) ................................. 2007-287880

(51) Int. Cl.
*B01L 1/00* (2006.01)
*G01N 33/487* (2006.01)
(Continued)

(52) U.S. Cl.
CPC .. *G01N 27/3272* (2013.01); *G01N 2035/00148* (2013.01)
USPC ........................ 204/403.01; 204/411; 204/412

(58) Field of Classification Search
CPC ......... B01L 1/00; B01L 3/5027; B01L 3/527; B01L 2400/0481; B01L 2400/0493; B01L 2400/0688; B01L 2400/086; B01L 2400/088; G01N 33/483; G01N 33/487; G01N 33/48707; G01N 33/49; G01N 33/491; G01N 33/492; G01N 15/05; G01N 31/20
USPC ........................ 204/403.01–403.15, 411, 412; 205/777.5, 778, 792; 435/4–40.52; 422/68.1–98; 436/62–71, 500–548
See application file for complete search history.

(56) References Cited

U.S. PATENT DOCUMENTS 5,407,806 A 4/1995 Yabuuchi et al.
5,426,033 A * 6/1995 Kojima et al. .................. 435/14
(Continued)

FOREIGN PATENT DOCUMENTS

EP 1118675 A2 7/2001
EP 1571443 A1 9/2005
(Continued)

OTHER PUBLICATIONS

International Search Report for International application No. PCT/JP2008/070095 with English translation mailed Jan. 13, 2009.
(Continued)

*Primary Examiner* — Susan D Leong
(74) *Attorney, Agent, or Firm* — Cantor Colburn LLP (57) ABSTRACT

A biosensor for electrochemically measuring a sample may include a first member made of an insulating material, an electrode system including a working electrode and a counter electrode formed on the first member, a second member fixed over the first member, a sample flow channel provided between the first member and the second member, a hydrophilic section provided on at least a part of the internal surface of the sample flow channel and extending from a first end near the electrode system to a second end on the opposite side, and a flow stop area provided on a section adjacent to the second end on the first member or on the internal surface of the sample flow channel.

13 Claims, 6 Drawing Sheets

(51) Int. Cl.
*G01N 31/20* (2006.01)
*B01L 3/00* (2006.01)
*G01N 27/327* (2006.01)
*G01N 35/00* (2006.01)

(56) References Cited

U.S. PATENT DOCUMENTS

| | | | | |
|---|---|---|---|---|
| 5,627,041 | A | * | 5/1997 | Shartle ............... 435/7.24 |
| 5,766,552 | A | * | 6/1998 | Doshi et al. ............. 422/535 |
| 7,611,621 | B2 | * | 11/2009 | Cai et al. ............. 205/777.5 |
| 8,691,161 | B2 | * | 4/2014 | Fleming ................ 422/412 |
| 2002/0064480 | A1 | * | 5/2002 | Shartle ................... 422/57 |
| 2002/0081588 | A1 | * | 6/2002 | De Lumley-woodyear et al. ........... 435/6 |
| 2003/0008401 | A1 | * | 1/2003 | Berndt ..................... 436/8 |
| 2003/0199744 | A1 | * | 10/2003 | Buse et al. ............... 600/347 |
| 2004/0067166 | A1 | * | 4/2004 | Karinka et al. ......... 422/82.03 |
| 2006/0043023 | A1 | * | 3/2006 | Srinivasan et al. ........ 210/659 |
| 2008/0006530 | A1 | * | 1/2008 | Winarta et al. ......... 204/403.01 |

FOREIGN PATENT DOCUMENTS

| | | |
|---|---|---|
| JP | 6-109693 A | 4/1994 |
| JP | 10-62402 A | 3/1998 |
| JP | 2000-221157 A | 8/2000 |
| JP | 2000-338076 A | 12/2000 |
| JP | 3267933 B2 | 1/2002 |
| JP | 2003-254934 A | 9/2003 |
| JP | 2004-245736 A | 9/2004 |
| JP | 2006-308561 A | 11/2006 |
| WO | 2006/134870 A1 | 12/2006 |

OTHER PUBLICATIONS

Japanese Office Action for Japanese Patent Application No. 2009-540054 mailing date of Mar. 27, 2012 with English translation.
European Search Report for Application No./Patent No. 08846754.3-1554/2211171 PCT/JP2008070095, dated Mar. 19, 2014.

* cited by examiner

BIOSENSOR

This is a U.S. national stage application of International Application No. PCT/JP2008/070095, filed on 5 Nov. 2008. Priority under 35 U.S.C. §119(a) and 35 U.S.C. §365(b) is claimed from Japanese Application No. JP2007-287880, filed 5 Nov. 2007, the disclosure of which is also incorporated herein by reference.

TECHNICAL FIELD

The present invention relates to a biosensor for easily measuring a substance in sample.

Priority is claimed on Japanese Patent Application No. 2007-287880, filed Nov. 5, 2007, the content of which is incorporated herein by reference.

BACKGROUND ART 1,5-anhydroglucitol (denoted as "1,5-AG" hereinafter) has gained attention in recent years as a marker for understanding the state of blood glucose control in diabetic patients. Specifically, 1,5-AG is useful as it is not readily affected by a food intake, but rather reflects blood glucose control over the relatively short period of the preceding week.

Biosensors which provide patients with self-regulation indicators are conventionally known. With these biosensors, the patient collects a sample of blood, etc., at home, sets the sample in the detection device, and then measures his blood glucose level, etc. on his own (see Patent Reference Document 1, for example). This biosensor is provided with an electrode connected to a detection device which is mounted on an insulated circuit board. The sample is supplied from a sample supply port, and then passes through a sample supplying channel to arrive at the electrode, where measurements can be conducted.

[Patent Reference Document 1] Japanese Patent Publication No. 3267933

DISCLOSURE OF THE INVENTION

Problems to be Resolved by the Invention

However, when the biosensor disclosed in Patent Reference Document 1 is employed for self-measurement of such biochemical markers in blood as 1,5-AG or the like, the following problems arise.

Namely, among biochemical markers in blood, there are many which require a two-step reaction process in which a pre-treatment reaction is first performed on the collected blood to remove interfering substances in the blood which would interfere with the detection reaction. After these substances have been removed, the detection reaction may be performed. For example, in the measurement of serum total bilirubin, a pre-treatment is performed using a surfactant, after which the detection reaction is carried out using the diazo reaction. In the measurement of creatinine, a method is known in which the creatine is removed in a pre-treatment, and then detected. In the measurement of the aforementioned 1,5-AG, the glucose is first removed, after which the 1,5-AG detection reaction is performed.

A specific amount of time is required in each of the pre-treatment reactions described above. However, in the biosensor disclosed in Patent Reference Document 1, the sample arrives at the electrode immediately after it is supplied via the sample supply port, making measurement of markers that require a pre-treatment reaction step difficult.

The present invention was conceived in view of the above-described circumstances and has as its objective the provision of a biosensor that enables easy control of the timing at which the collected sample is transferred to the testing site.

Means for Resolving the Problem

The present invention is a biosensor for electrochemically measuring a sample, characterized in the provision of a first member made of an insulating material; an electrode system including a working electrode and a counter electrode formed on the first member; a second member fixed over the first member so as to cover at least a part of the electrode system; a sample flow channel provided between the first member and the second member to allow communication between the outside and a part of the electrode system covered by the second member; a hydrophilic section provided on at least a part of the internal surface of the sample flow channel and extending from a first end near the electrode system to a second end on the opposite side; and a flow stop area provided on a section adjacent to the second end on the first member or on the internal surface of the sample flow channel to temporarily stop the flow of the sample into the electrode system.

In the biosensor according to the present invention, the sample is temporarily stopped by the flow stop area. As a result, in the biosensor according to the present invention, it is possible to control of the timing at which a sample reaches the electrode system, which is the site of measurement.

The biosensor according to the present invention may be further equipped with a sample retaining area which is provided to the first member and is for retaining the sample which has been dripped down. In this case, the sample can be retained in a stable state on the first member.

The aforementioned flow stop area may be a linear or belt-shaped hydrophobic section which is provided to the internal surface of the sample flow channel so as to transect the hydrophilic section in the width direction of the sample flow channel. The flow stop area can be easily formed in this case.

Further, the flow stop area may be formed of a linear or belt-shaped hydrophobic section which is provided between the sample retaining area and the second end so as to stop the sample in a state where it is not contacting the sample flow channel. In this case, the sample retaining area can be utilized as a site for performing pre-treatment reactions.

The sample retaining area may be formed to have a hydrophilic surface, with a step formed to the first member so that the step is higher than the other areas of the first member. It is possible to hold the sample more stably in this case.

The hydrophobic section may have a convex section in which the convexity is directed toward the electrode system. In this case, the sample converges toward the convex section making it easier to pass over the hydrophobic section. As a result, operating timing control of the sample flow is facilitated.

The present invention's biosensor may be further provided with an introduced piece which is provided extending from the second end side of the sample flow channel of the second member, and a second hydrophilic section which is provided on the surface of the introduced piece which faces the first member, and which connects with the aforementioned hydrophilic section. It is easier to introduce the sample into the flow channel in this case.

The introduced piece is formed of a material having elasticity which can be bent so as to move away from the first member. In this case, it becomes easier to place the sample below the introduced piece.

The portion of the first member that is opposite the introduced piece may be designed to have the same shape as the introduced piece, with the sample flowing up to the flow stop area once the sample is brought into contact with the introduced piece. In this case, the sample is introduced into the sample flow channel by bringing the introduced piece into contact with the sample which is on the patient's skin, in a reaction container, etc.

A plurality of electrode systems may be provided on the first member, with sample flow channels provided for these respective electrode systems. It is possible to form a biosensor capable of carrying out measurements using a differential method in this case.

The second member may be fixed in place to the first member via a spacer which is provided between the first member and the second member, and the side wall of the sample flow channel may be formed from this spacer. The fixation of the second member and the design of the shape of the sample flow channel can be easily carried out in this case.

Note that the term "side wall" indicates from among the wall surfaces of the sample flow channel, the wall surface which is provided between the first member and the second member.

A pre-treatment reagent may be placed to at least one of either an area of the sample flow channel that is farther toward the second end than the flow stop area, or an area on the first member which is not covered by the second member, this pre-treatment reagent being employed in a pre-treatment reaction on the sample in order to remove, capture or convert to an inert form interfering substances which would hinder the electrochemical measurement.

In this case, pre-treatment of the sample using the pre-treatment reagent can be performed while the sample is stopped at the area before the flow stop area. Thus, it is possible to form a biosensor that is capable of accurate measurements even in the case of a measurement marker for which interfering substances are present in the blood.

Note that in addition to reagents that cause chemical reactions, the term "pre-treatment reagent" also includes microbeads for capturing specific substances using ion adsorption, affinity adsorption or adsorption as boric acid complexes.

An oxidoreductase and redox mediator may be disposed to the working electrode in the electrode system.

The aforementioned redox mediator includes at least one of ruthenium derivative, osmium derivative, ferrocyanide derivative, ferrocene derivative, quinone derivative, phenothiazine derivative, phenoxazine derivative, phenazine derivative, indophenol derivative, diphenylamine derivative or phenol derivative.

The aforementioned oxidoreductase includes at least one of pyranose oxidase, L-sorbose oxidase, 1,5-AG dehydrogenase, L-sorbose dehydrogenase and the like.

The aforementioned pre-treatment reagent includes reagent for removing, capturing or converting glucose to another substance which does not effect the electrochemical measurement.

In these cases, it is possible to form a biosensor for measuring 1,5-AG capable of optimal measurement of 1,5-AG.

Effects of the Invention

The biosensor according to the present invention enables easy control of the timing at which a collected sample is transitioned to the testing site.

EXPLANATION OF THE SYMBOLS

1, 21, 31, 41, 51 biosensor
2, 32 circuit board (first member)
3 electrode system
3A, 52B, 53B counter electrode
3B, 52A, 53A working electrode
4, 57 cover member (second member)
5, 42 sample retaining area
7, 56 double-sided adhesive tape (spacer)
8, 44 sample flow channel
9, 61 introduced piece
10 first hydrophilic section (hydrophilic section)
11 second hydrophilic section
12, 45, 60, 60A, 60B hydrophobic section (flow stop area)
13 pre-treatment reagent

BEST MODE FOR CARRYING OUT THE INVENTION

Figure 1:
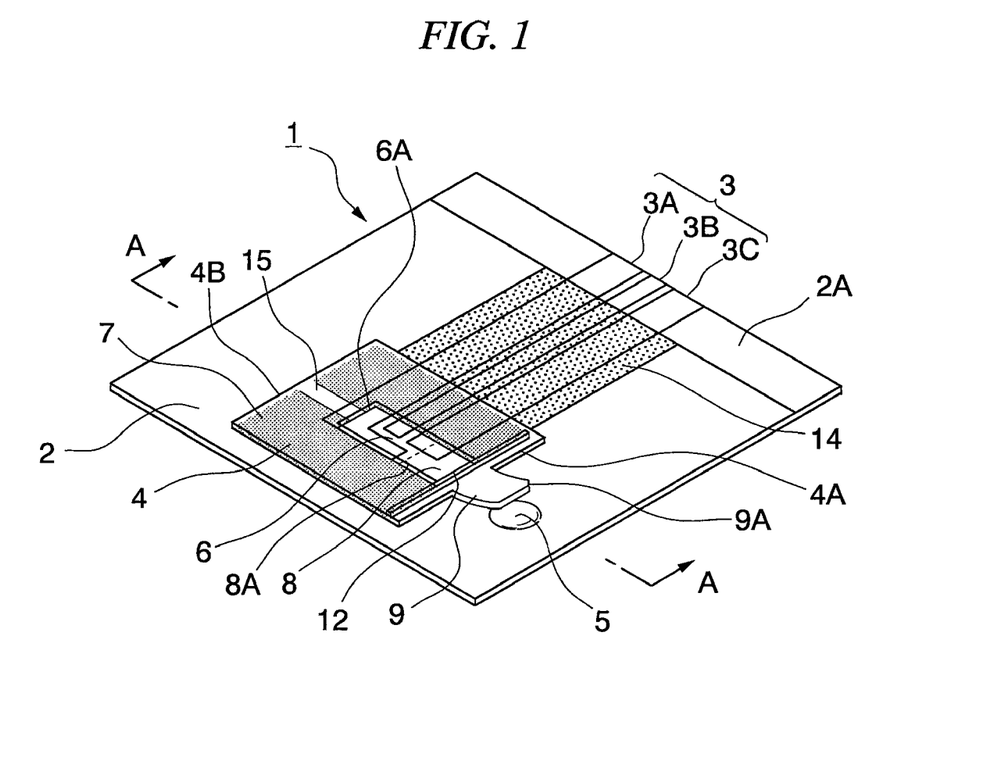
FIG. 1 is a perspective view of the biosensor according to the first embodiment of the present invention.

The biosensor according to a first embodiment of the present invention will now be explained with reference to FIGS. 1 through 3. The biosensor in the various examples below, including the present embodiment, is a 1,5-AG measurement biosensor for measuring 1,5-AG. As shown in FIG. 1, the biosensor 1 is provided with a circuit board (first member) 2 consisting of an insulating material, an electrode system 3 provided to one side of the circuit board 2, and a cover member (second member) 4 which is fixed to the circuit board 2 so as to cover a portion of the electrode system 3.

The circuit board 2 is a plate-shaped member, with one end forming an inserted part 2A which is inserted into the detection device. The insulating material forming the circuit board 2 is not particularly restricted as long as it has insulating properties and the required strength. For example, plastic film or the like may be used. The plastic film is not particularly limited as long as it can be formed into a film which has a macromolecular compound as its main component. Preferred examples of macromolecular compounds include polyethylene terephthalate (PET), polyethylene naphthalate (PEN), polycarbonate (PC), polyacrylate, polyethersulfone (PES), polyimide, polyamide, polypropylene (PP), polyethylene (PE), cyclo-olefin polymer (COP), polymethylmethacrylate (PMMA), polydimethylsiloxane (PDMS), triacetyl cellulose (TAC), diacetyl cellulose (DAC), polystyrene (PS), polyurethane, polyvinyl alcohol (PVA), EVAL (ethylene vinyl alcohol copolyer), polyvinyl chloride (PVC), and the like. It is also acceptable to employ glass or the like. Among these, however, PET is preferred for its easy handling.

A sample retaining area 5, which is a substantially circularly shaped concavity, is formed in the circuit board 2. The sample drips into this sample retaining area 5 and is temporarily held there prior to measurement. In this embodiment, the sample retaining area 5 and its surrounding periphery have a hydrophobic surface having hydrophobic properties. When the circuit board 2 is formed of a material which does not have hydrophobic properties, then hydrophobic properties may be conferred by means of a coating layer, as will be explained below. Note that it is also acceptable to provide hydrophilic properties using a hydrophilic treatment or the like, in place of applying hydrophobic properties to the sample retaining area 5.

The size, shape, depth, etc. of the sample retaining area 5 may be suitably designed according to the sample to be used. The position at which the sample retaining area 5 is provided may be optionally set. However, it is convenient during use if the sample retaining area is provided near the sample flow channel. In addition, as necessary, a sample detection electrode may be provided which extends from within the sample retaining area 5 to the inserted part 2A, connecting with the detection device, in order for the detection device into which the biosensor 1 is inserted to detect the presence of the sample in the sample retaining area.

The electrode system 3 has a counter electrode 3A, a working electrode 3B and a reference electrode 3C. These various electrodes 3A, 3B and 3C are formed onto the circuit board 2 using a screen printing method or the like employing a conductive carbon ink. The electrode system 3 is provided extending to the inserted part 2A. The electrode system 3 is connected to the detection device when the inserted part 2A is inserted into the detection device.

In addition to carbon, various materials such as gold, platinum, palladium or silver, silver/silver chloride, nickel, copper, titanium, iridium, lead, tin oxide, platinum black and the like may be used as the material for forming the electrode system 3. In place of a screen printing method, it is also acceptable to form the electrode system using various types of vapor deposition methods such as a vacuum or ion plating method, or by means of a sputtering method, foil stick method, electroplating method, etc. In addition, in place of directly forming the electrode system 3 onto the circuit board 2, it is also acceptable to form the electrode system 3 in which an electrode member is made by forming a metal foil or the like to another base, and fixing this to the circuit board 2 using an adhesive or the like. The action of the electrode system 3 will be described below.

The substantially square region which includes the ends of the various electrodes 3A, 3B and 3C of the electrode system 3 that are on the opposite side from the inserted part 2A is designated as test area 6, where contact is made with the sample. A reagent, which is not shown in the figure, for enabling electrochemical measurements by reacting with the sample is disposed using a method such as dipping or spin coating.

Note that a shape of the test area 6 may not be particularly restricted to be the substantially square region. Rather, various shapes may be employed for the shape of the test area 6 such as circular or oval shapes so long as a collected sample can be easily measured.

The content of the reagent may be suitably determined according to the reaction that is to occur at the test area 6. For example, in a measurement, etc., which directly detects hydrogen peroxide, it is acceptable to place only oxidase. In the case of a substance which does not require a particular reaction to enable measurement, such as sodium ion, potassium ion or the like, it is not necessary to provide a reagent. In the biosensor 1 according to this embodiment, a redox enzyme which can oxidize 1,5-AG and a redox mediator which serves as an intermediary for exchanging the electrons participating in the redox reaction are provided.

Examples of 1,5-AG redox enzymes include pyranose oxidase, L-sorbose oxidase, 1,5-AG-dehydrogenase, L-sorbose dehydrogenase, and the like.

Examples of redox mediators include ruthenium derivative, osmium derivative, ferrocyanide derivative, ferrocene derivative, quinone derivative, phenothiazine derivative, phenoxazine derivative, phenazine derivative, indophenol derivative, diphenylamine derivative, phenol derivative and the like. Specific examples of products with may be employed include [ruthenium (bipyridyl)$_2$ imidazoyl Cl]Cl$_2$, polyvinylimidazoly and complexed [ruthenium (bipyridyl)$_2$ imidazoyl Cl], [osmium (bipyridyl)$_2$ imidazoyl Cl]Cl$_2$, polyvinylimidazoly and complexed [osmium (bipyridyl)$_2$ imidazoyl Cl], potassium ferricyanide, sodium ferricyanide, ferrocene, ferrocene methanol, ferrocene PEG, benzoquinone, 2,6-dimethyl benzoquinone, thionin, methylene blue, toluidine blue-O, azur I, azur C, azur A, 1-methoxyphenazine methosulfate, safranine, phenosafranine, 2-dichlorophenol indophenol (DCIP), 4,4'-bis(dimethylamino)diphenylamine, p-aminophenol and the like.

Figure 2:
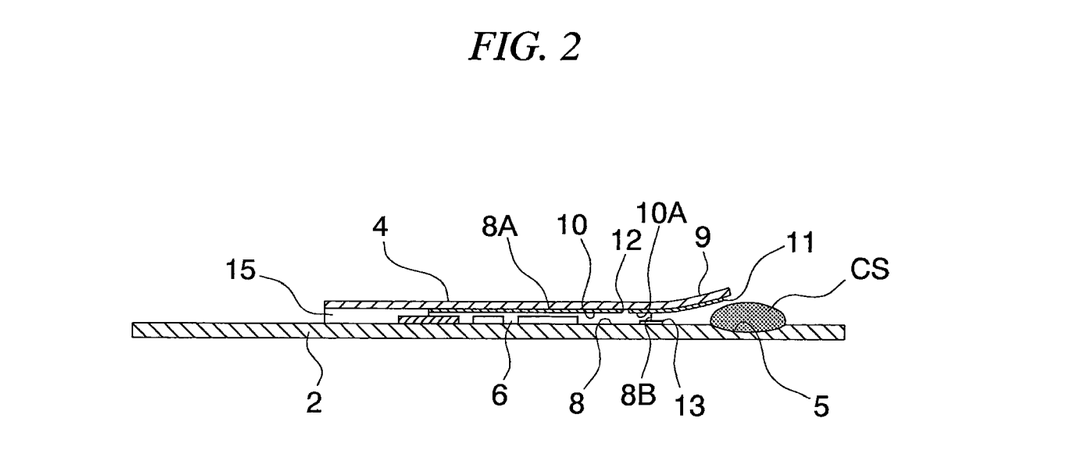
FIG. 2 is a cross-sectional view along the line A-A in FIG. 1.
Figure 3A:
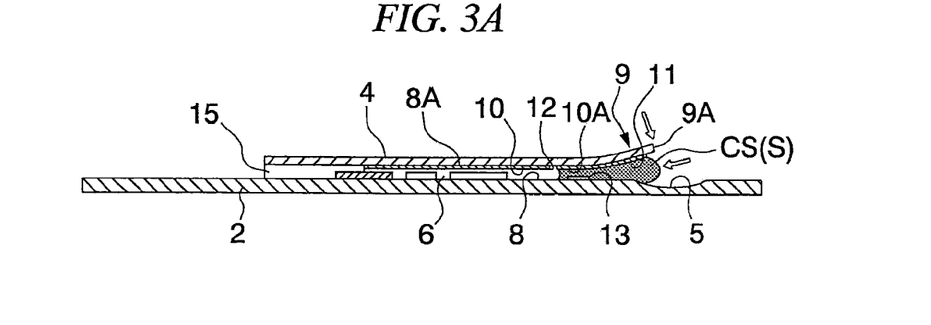
FIG. 3A is a view showing the state in which sample flow has been stopped in the biosensor according to the first embodiment.

FIG. 2 is a cross-sectional view along the line A-A in FIG. 1. The cover member 4 is formed of a material such as resin which has elasticity, and is attached on to the circuit board 2 via double-sided adhesive tape (spacer) 7 so as to cover the test area 6 which includes part of the electrode system 3. A portion of the double-sided adhesive tape 7 that is on test area 6 has been removed, as has a portion of a specific width extending from the test area 6 to the end 4A of the cover member 4. As a result of this design, the test area 6 which is covered by cover member 4 communicates with the outside, and the sample flow channel 8 through which the sample is introduced to the test area 6 of the electrode system 3 is formed of the double-sided adhesive tape 7, the circuit board 2, and the cover member 4. In other words, in the arrangement shown in FIGS. 1 and 2, the bottom surface of the sample flow channel 8 is formed by the circuit board 2, and the top surface of the sample flow channel 8 is formed by the cover member 4. The other wall surfaces (side walls), which are substantially perpendicular to the circuit board 2 and the cover member 4, are formed by the double-sided adhesive tape 7.

Note that in the sample flow channel 8, the first end 8A communicates with the test area 6 and the opposing second end 8B communicates with the outside not covered by the cover member 4.

Further, a portion of the double-sided adhesive tape 7 is cut away in a linear strip extending from the end 6A on the opposite side of the sample flow channel 8 of the test area 6, to the end 4B of the cover member, to form an air outlet 15. The air outlet 15 serves the function of releasing the air inside the sample flow channel 8 and the test area 6 when the sample is moving within the sample flow channel 8 toward the test area 6.

A substantially square-shaped introduced piece 9 is provided to the cover member 4 extending from its end 4A that is on the side where the sample flow channel 8 opens. The introduced piece 9 is provided with a length that extends sufficiently so that the front end 9A reaches above the sample retaining area 5. The front end 9A is bent to be directed substantially upward, separating away from the circuit board 2.

A first hydrophilic section (hydrophilic section) 10 having hydrophilic properties is provided to the surface of the cover member 4 above the sample flow channel 8 which is opposite the circuit board 2, this first hydrophilic section 10 reaching from the second end 8B of the sample flow channel 8 on the end 4A side of the cover member 4 through the first end 8A on the electrode 3 side to within the test area 6.

The first hydrophilic section 10 may be formed by using a coating method or the like to fix a hydrophilic substance such as a hydrophilic polymer or hydrophilic coating to the cover member 4 which is formed of a resin or the like. It is also acceptable to add hydrophilic properties by performing a plasma treatment to the surface of the cover member 4. Further, the cover member 4 may be provided by forming it using a hydrophilic plastic sheet such as GelBond Film (Cambrex Corp.), Hydrotect Film (Toto Ltd.), ARcare 8877 (Adhesives Research, Inc.), etc.

Note that it is preferable to provide the first hydrophilic section 10 in a continuous linear or belt-like shape. However, as long as the sample can be guided into the test area 6 without problem, then it is also acceptable for the first hydrophilic section 10 to be in the form of a dashed line, with only a small spacing interval.

A second hydrophilic section 11 is provided to the surface of the introduced piece 9 which is opposite the circuit board 2 so as to be linked with the first hydrophilic section 10 which is provided to the sample flow channel 8. The second hydrophilic section 11 can be formed using the same method as that employed for the first hydrophilic section 10.

A belt-shaped hydrophobic section (flow stop area) 12 having hydrophobic properties is provided near the end 10A on the introduced piece 9 side of the first hydrophilic section 10, so as to extend across the width of the sample flow channel 8 and transect the first hydrophilic section 10. The hydrophobic section 12 has the function of temporarily stopping the flow of the sample toward the test area 6.

It is acceptable to provide the hydrophobic section 12 by fixing a hydrophobic material in place on the first hydrophilic section 10 using a method such as coating or the like, or by exposing the hydrophobic cover member 4 by partially removing the first hydrophilic section 10. Further, the hydrophobic section 12 may be formed to have a linear shape, provided that this is capable of stopping the flow of the sample.

Using a coating and drying or a screen printing method, a pre-treatment reagent 13 is fixed in place to the sample flow channel 8 farther toward the introduced piece 9 side than the hydrophobic section 12. This pre-treatment reagent 13 is for use in a pre-treatment reaction to break down, remove, capture or electrochemically convert into an inert substance the glucose in a sample which would impair the measurement of 1,5-AG An enzyme which is active in breaking down or converting glucose is included in the pre-treatment reagent 13 in this embodiment.

Specifically, in the case where oxidizing glucose, examples including mixtures such as glucose oxidase or glucose dehydrogenase and the co-enzymes nicotinamide adenine dinucleotide (NAD), nicotinamide adenine dinucleotide phosphate NADP, pyrroloquinoline quinone (PQQ) or the like may be cited. Examples which may be cited for phosphorylating glucose are those including hexokinase or glucokinase and ATP and the like.

Note that the content of the pre-treatment reagent 13 may be suitably varied depending on the required pre-treatment reaction. The content of the pre-treatment reaction is not particularly restricted. Rather, in addition to various reactions such as decomposition, removal, conversion, etc., a variety of pre-treatment reactions may be carried out so long as the reaction is possible in the biosensor, such as ion adsorption, affinity adsorption or adsorption using microbeads that employ as boric acid complexes.

The portion of the electrode system 3 that is not covered by the cover member 4 remains in the vicinity of the inserted part 2A of the circuit board 2 and is covered by a cover layer 14 which has insulating properties. The coating layer 14 can be formed by coating a heat or UV curable insulating coating material to the circuit board 2 and the electrode system 3 using screen printing.

The operation of measuring 1,5-AG using a biosensor 1 designed as described above will now be explained with reference to FIGS. 2 and 3.

First, the user sets the inserted part 2A of the biosensor 1 into the detection device.

Next, as shown in FIG. 2, the user drips a whole blood sample (test sample) CS obtained from the finger, etc. onto the sample retaining area 5. Since the circuit board 2 has hydrophobic properties, the dripped whole blood sample CS is substantially spherical due to surface tension.

Under these conditions, when the user pushes the end 9A of the introduced piece 9 from above, the whole blood sample CS and the second hydrophilic section 11 provided to the introduced piece 9 come into contact. Further, the whole blood sample CS travels through the second hydrophilic section 11 and the first hydrophilic section 10 which connects with the second hydrophilic section 11 and flows toward the test area 6. However, the flow temporarily stops due to interference from the hydrophobic section 12 which has hydrophobic properties.

Running parallel to this flow, the whole blood sample CS comes in contact with the pre-treatment reagent 13 which is fixed to the sample flow channel 8, and the reaction of breaking down or converting the glucose in the whole blood sample CS is initiated. Once a specific time period has elapsed during which the whole blood sample CS is stopped at the hydrophobic section 12, the breakdown, removal capture or conversion of the glucose to an inert substance which does not affect the electrochemical reaction is completed. The whole blood sample CS is thus rendered into the measurement sample (sample) S on which measurement preparations have been finished.

Figure 3B:
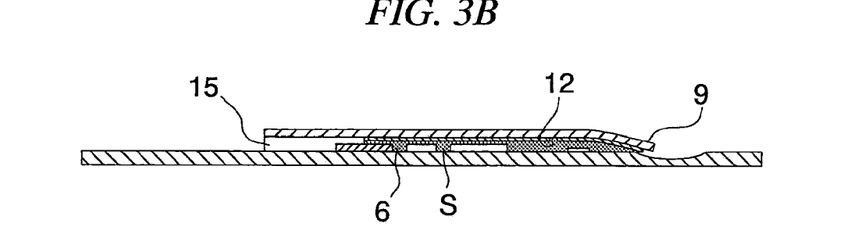
FIG. 3B is a view showing the state in which the sample has been introduced into the electrode system in the biosensor according to the first embodiment.

As shown in FIG. 3B, as a result of the user pushing the test sample S into the sample flow channel 8 or the detection device automatically introducing the test sample S into the sample flow channel 8 through suction or pressure, the test sample S surpasses the hydrophobic section 12 and comes into contact with the first hydrophilic section 10 on the test area 6 side. Next, the test sample S travels through the hydrophilic section 10 and reaches the test area 6.

The test sample S introduced into the test area 6 undergoes a conventional reaction such as a redox reaction with the reagent which is disposed in the test area 6. Then, a voltage is impressed on the electrode system 3 of the biosensor 1 from the detection device to measure the current value. As a result, the concentration of 1,5-AG is measured.

In the biosensor 1 according to the present embodiment, the sample travels though the hydrophilic section 11 provided to the introduced piece 9 simply by pressing the introduced piece 9 from above to bring it into contact with the sample in the sample retaining area 5. As a result, it is possible to more easily introduce the sample into the sample flow channel 8.

The flow of the sample inside the sample flow channel 8 is temporarily stopped by the hydrophobic section 12, allowing the sample to react with the pre-treatment reagent 13. Next, by pushing away from the hydrophobic section 12, the sample comes into contact with the first hydrophilic section 10 of the sample flow channel 8, enabling the release of the stopped state. As a result, the sample can be relayed to the test area 6 by regulating timing for reaching the test area 6 by means of an easy operation.

Further, the introduced piece 9 bends so as to move away from the circuit board 2. As a result, the sample can be easily disposed below the introduced piece 9 and guidance of the sample into the sample flow channel can be easily carried out.

In addition, the pre-treatment reagent 13 is disposed farther toward the introduced piece 9 side than the hydrophobic section 12. As a result, it is possible to carry out the pre-treatment reaction on the sample by reacting the whole blood sample CS with the pre-treatment reagent 13 while the pre-treatment whole blood sample CS is in the stopped state on the upstream side of the hydrophobic section 12. Accordingly, the necessity to carry out pre-treatment of the sample using a separate reaction container or the like prior to dripping the sample into the biosensor 1 is eliminated. Further, even in the case where it is necessary to carry out a detection process in addition to the pre-treatment reaction external to the biosensor, it is possible to simplify the aforementioned process by separating the pre-treatment reaction and the detection process. Thus, the work accompanying the measurement can be reduced and the measurement of 1,5-AG can be carried out more easily.

The cover member 4 is attached to the circuit board 2 using double-sided adhesive tape 7. Accordingly, the cover member 4 can be fixed in place to the circuit board 2 easily. Further, by simply modifying the shape of the double-sided adhesive tape 7, it is possible to easily change the shape of the test area 6 and the sample flow channel 8. As a result, it is possible to easily form the biosensor appropriate to a variety of measurement conditions. Further, since the circuit board 2 and the sample retaining area 5 have hydrophobic properties, the dripped in whole blood sample CS flows naturally, and does not have contact with the sample flow channel 8. Accordingly, it is possible to avoid introduction of the sample into the test area 6 at a timing unintended by the user.

Note that this embodiment explained an example in which the pre-treatment reagent 13 was fixed to the sample flow channel 8. However, in place of this, it is also acceptable to fix the pre-treatment reagent 13 to the sample retaining area 5 using a method such as fixing the pre-treatment reagent 13 to the sample retaining area 5 using a dipping or spin coating method, attaching dried filter paper impregnated with the pre-treatment reagent 13, disposing the pre-treatment reagent as a soluble film, or disposing microbeads or other such carrier into which an active group has been introduced. In this case, the whole blood sample CS is dripped into the sample retaining area 5 and retained for a specific period of time, thereby enabling the pre-treatment reaction on the whole blood sample CS to be performed. Note that when the pre-treatment reagent 13 is fixed to the sample flow channel 8, fixing may be performed by a method such as introduction of an ion exchange group into the sample flow channel 8.

Figure 4:
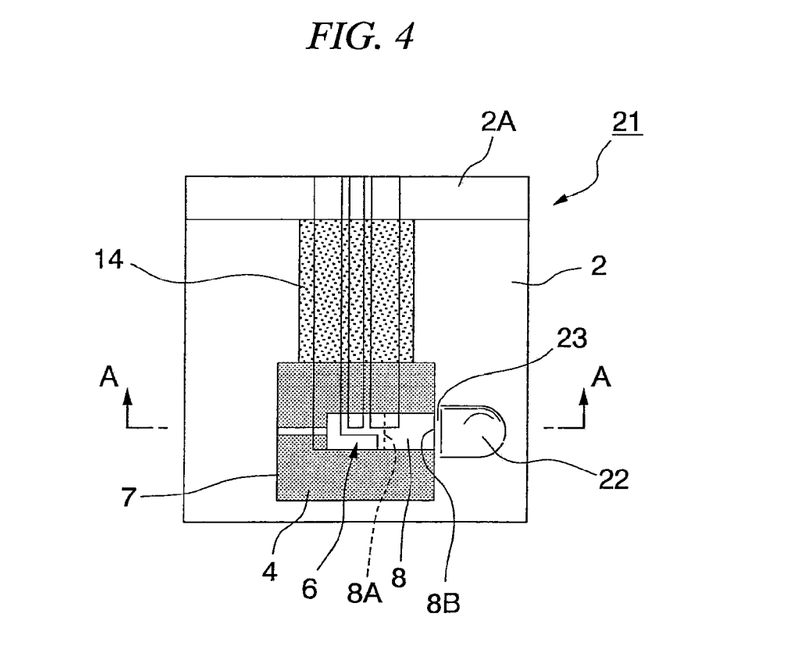
FIG. 4 is a plan view showing a modification of the biosensor according to the first embodiment.

The present embodiment explained an example in which a hydrophobic section 12 was provided inside the sample flow channel 8. However, in place of this, as in the biosensor 21 of the modification shown in FIG. 4, the circuit board 2 (or a coating layer 14, etc. provided on the circuit board 2) which is adjacent to the second end 8B of the sample flow channel 8 may function as a hydrophobic section 23 for temporarily stopping the flow of the sample from the sample retaining area 22 to the test area 6. As a result of this design, it is possible to provide a flow stop area which is external to the sample flow channel 8. Accordingly, this facilitates the formation of the cover member 4 and improves the production efficiency of the biosensor.

This embodiment explained an example in which a coating layer 14 was only provided to the top surface and periphery of the electrode system 3. However, in place of this, it is also acceptable to coat the entirety of the section not covered by cover member 4 with the coating layer 14, excluding the inserted part 2A. In this case, in order to ensure the hydrophobic properties of the sample retaining area 5 and its vicinity, it is preferable to form the coating layer 14 from a hydrophobic material.

This embodiment explained an example in which the sample retaining area 5 was formed by providing a concavity in the circuit board 2. However, in place of this, it is also acceptable to form the sample retaining area 5 by covering the entire upper surface of the circuit board 2, excluding one area, with the coating layer 14, and the exposing the circuit board 2 as a hydrophobic surface in the aforementioned area.

The present embodiment explained a biosensor for measuring 1,5-AG. However, by changing the reagent which is disposed in the electrode system and the design of the pre-treatment reagent 13 according to the reaction details of the required pre-treatment, the biosensor according to the present embodiment can be widely applied to other markers which require pre-treatment of the sample.

Next, a second embodiment of the present invention will be explained with reference to FIGS. 5 and 6, using the measurement of 1,5-AG as an example. The biosensor 31 of this embodiment and the biosensor 1 discussed above differ with respect to the shape of the circuit board.

Note that the same numeric symbol will be applied to structural elements that are the same as those of the biosensor 1 of the first embodiment above, and a redundant explanation thereof will be omitted.

Figure 5:
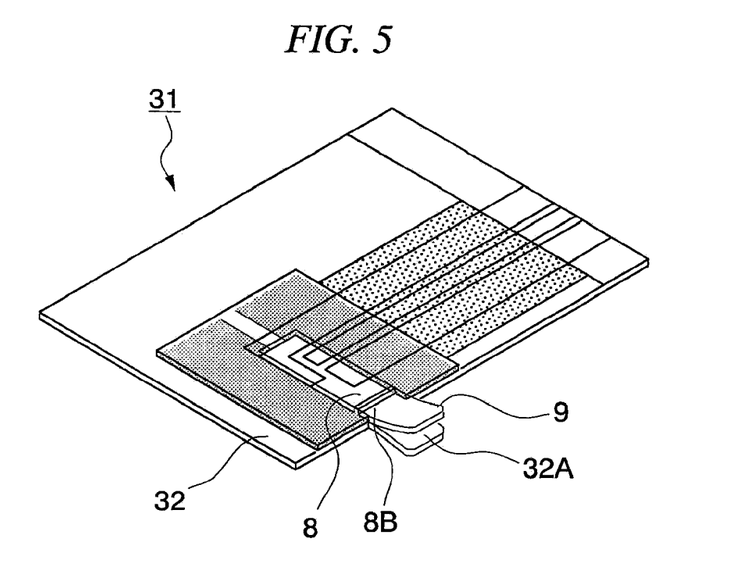
FIG. 5 is a perspective view of the biosensor according to the second embodiment of the present invention.

FIG. 5 is a perspective view of the biosensor 31. As shown in FIG. 5, a sample retaining area 5 is not provided to the circuit board 32 of the biosensor 31, and the second end 8B side of the sample flow channel 8 is cut away to leave an introduction circuit board 32A having substantially the same shape as the introduced piece 9. In other words, the introduction circuit board 32A, which is the portion of the circuit board 32 opposite the introduced piece 9, is formed to have substantially same shape as the introduced piece 9 projecting out from the second end 8B of the sample flow channel 8.

Figure 6:
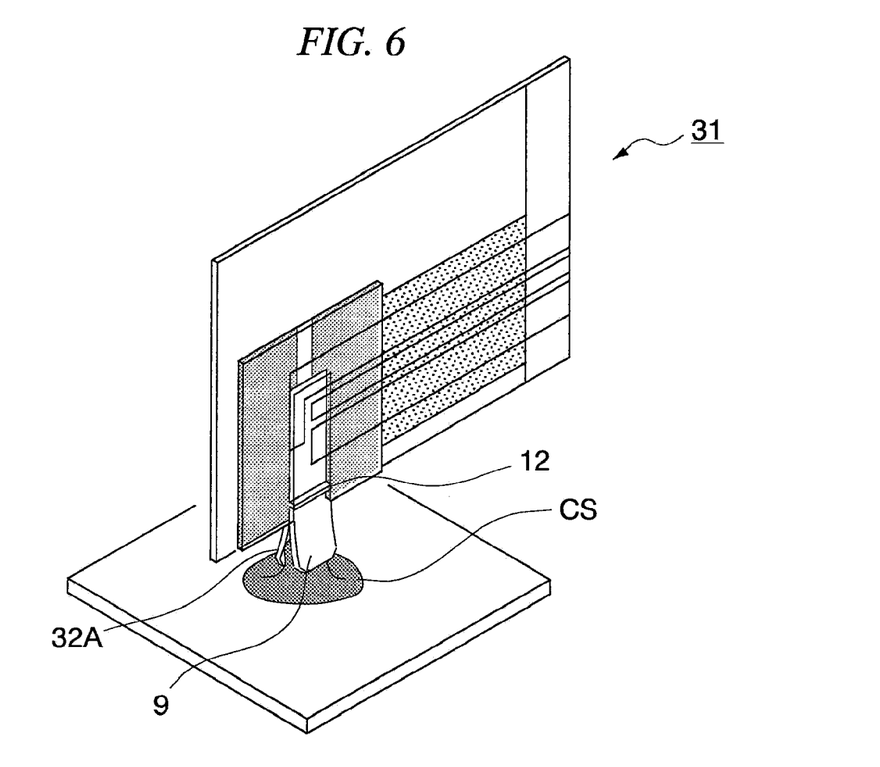
FIG. 6 is a view showing the state during use of the biosensor according to the second embodiment.

FIG. 6 is a view showing conditions during use of the biosensor 31. As shown in FIG. 6, when the user brings the introduced piece 9 and the introduction circuit board 32A closer together and into contact, the whole blood sample CS is drawn up between the introduced piece 9 and the introduction circuit board 32A as a result of the force which is communicated through the second hydrophilic section 11 (not shown in the figures) of the introduced piece 9 and the capillary phenomenon which is generated between the introduction circuit board 32A and the introduced piece 9.

The drawn up whole blood sample CS is temporarily stopped by the hydrophobic section 12. There, the pre-treatment reagent 13 and the whole blood sample CS react, causing the glucose concentration to fall, thereby creating the test sample S form the whole blood sample CS.

In the biosensor 31 according to this embodiment, the introduced piece 9 and the introduction circuit board 32A are brought into contact with a sample on the skin or inside another reaction vessel, so that the uptake of the sample into the sample flow channel 8 can be carried out easily. Accordingly, it is possible to make a biosensor that is easier to use.

Further, since it is not necessary to provide a sample retaining area to the circuit board 32, the work process for the circuit board 32 becomes simpler so that it can be easily formed.

This embodiment explained an example in which the introduced piece 9 and the introduction circuit board 32A were formed to be substantially square-shaped. However, in place of this, it is also acceptable is form the introduced piece 9 and the introduction circuit board 32A to be substantially pentagonal or triangular in shape, so that the distal ends of the introduced piece 9 and the introduction circuit board 32A (i.e., the ends opposite the second end 8B of the sample flow channel 8) narrow. As a result of this design, it becomes easier to bring the introduced piece 9 and the introduction circuit board 32A into contact with the sample.

Next, a third embodiment of the present invention will be explained with reference to FIGS. 7 and 8, using the measurement of 1,5-AG as an example. The shapes of the sample retaining area and the flow stop area are the points of difference between the biosensor 41 of this embodiment and the biosensor 1 discussed above.

Note that the same numeric symbol will be applied to structural elements that are the same as in the biosensors of the preceding embodiments, and a redundant explanation thereof will be omitted.

Figure 7:
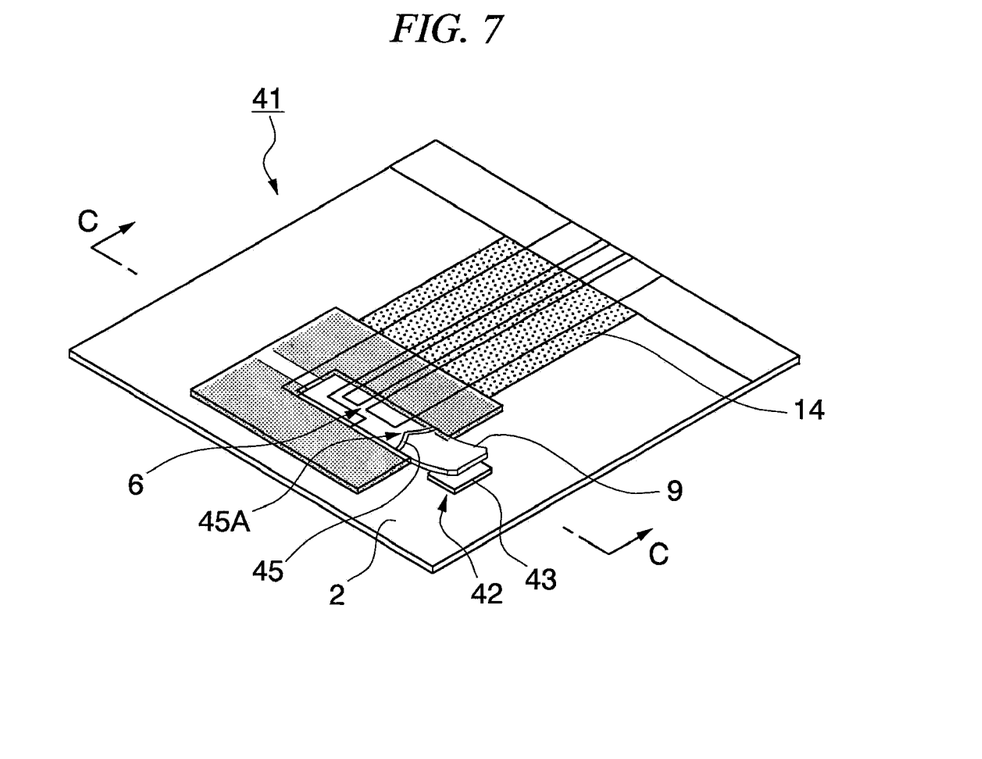
FIG. 7 is a perspective view of the biosensor according to the third embodiment of the present invention.
Figure 8:
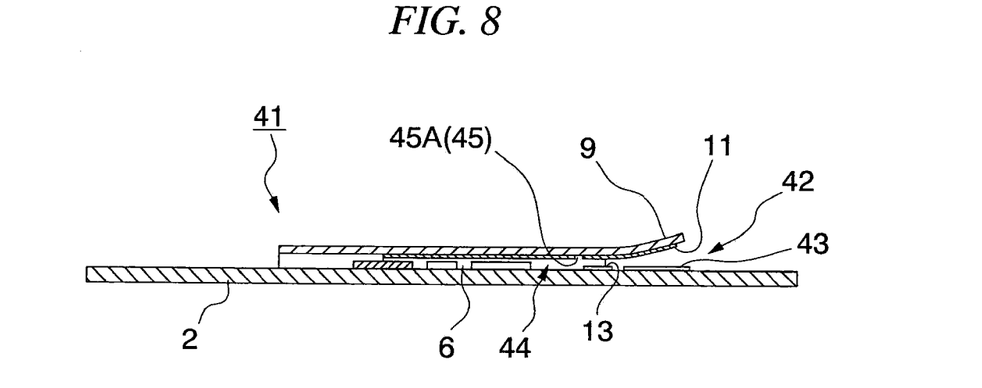
FIG. 8 is a cross-sectional view along the line C-C in FIG. 7.

FIG. 7 is a perspective view of the biosensor 41. FIG. 8 is a cross-sectional view along the line C-C in FIG. 7.

As shown in FIG. 7, the sample retaining area 42 of the biosensor 41 is fixed in place onto the circuit board 2 which is below the introduced piece 9 using a method in which a plate-shaped retaining member 43 which has a hydrophilic surface is adhered or fused. A method equivalent to that for forming the hydrophilic section to the sample flow channel described above may be employed as the method for forming the hydrophilic surface to the surface of the retaining member 43. By disposing a retaining member 43, the sample retaining area 42, which is one step higher than the surrounding circuit board 2 can be formed below the introduced piece 9.

Further, the hydrophobic section 45 which is provided to the sample flow channel 44 is formed to have a substantially V-shape having a convex section 45A, with the convexity directed toward the test area 6.

The operation of the biosensor 41 formed as described above will now be explained. The sample retaining area 42 has hydrophilic properties, while the surrounding circuit board 2 has hydrophobic properties. As a result, a dripped whole blood sample spreads in the shape of the surface area of the sample retaining area 42 and is retained without spreading out from the sample retaining area 42.

When the introduced piece 9 is brought into contact with the sample, then, as in the case of the biosensor 1 according the first embodiment, the whole blood sample is temporarily stopped in front of the hydrophobic section 45 and reacts with the pre-treatment reagent 13.

Once the reaction is done, the user presses on the introduced piece 9 or the hydrophobic section 45 and then releases, causing the reacted test sample to progress toward the hydrophobic section 45. At this time, the test sample moves so as to converge toward the convex section 45A of the hydrophobic section 45 which has the convexity directed toward the test area 6. The test sample surpasses the hydrophobic section 45 at the convex section 45A and moves toward the test area 6.

In the biosensor 41 according to this embodiment, the sample retaining area 42 is formed to be one step higher than the surrounding circuit board. As a result, it is easier to bring the introduced piece 9 into contact with the sample that is retained on the sample retaining area 42. Further, because the sample retaining area 42 has hydrophilic properties, while the surrounding circuit board 2 has hydrophobic properties, the sample can be stably spread over the entirety of the sample retaining area 42. As a result, the sample can be easily moved to the sample flow channel 44. Further, since the sample retaining area 42 has hydrophilic properties, the pre-treatment reagent 13 can be disposed uniformly on the top surface of the sample retaining area 42 and pre-treatment can be performed on the whole blood sample.

In addition, since the hydrophobic section 45 has a convex section 45A, the sample which is stopped in front of the hydrophobic section 45 converges toward the convex section 45A when the introduced piece 9 or the hydrophobic section 45 is pressed and then released. Accordingly, the sample can easily surpass the hydrophobic section 45 by means of a small pushing pressure, making it possible to form an easy-to-operate biosensor.

Further, the sample retaining area 42 can be formed by simply attaching a retaining member 43 to the circuit board 2. Thus, the work process for the circuit board 2 becomes simple, enabling an easy-to-produce biosensor.

Next, a fourth embodiment of the present invention will be explained with reference to FIGS. 9 through 11, using the measurement of 1,5-AG as an example. The biosensor 51 of this embodiment and the biosensor 1 discussed above differ with respect to the design of the electrode system and the fact that a plurality of electrode systems are provided in the former.

Note that the same numeric symbol will be applied to structural elements that are the same as in the biosensors of the preceding embodiments, and a redundant explanation thereof will be omitted.

Figure 9:
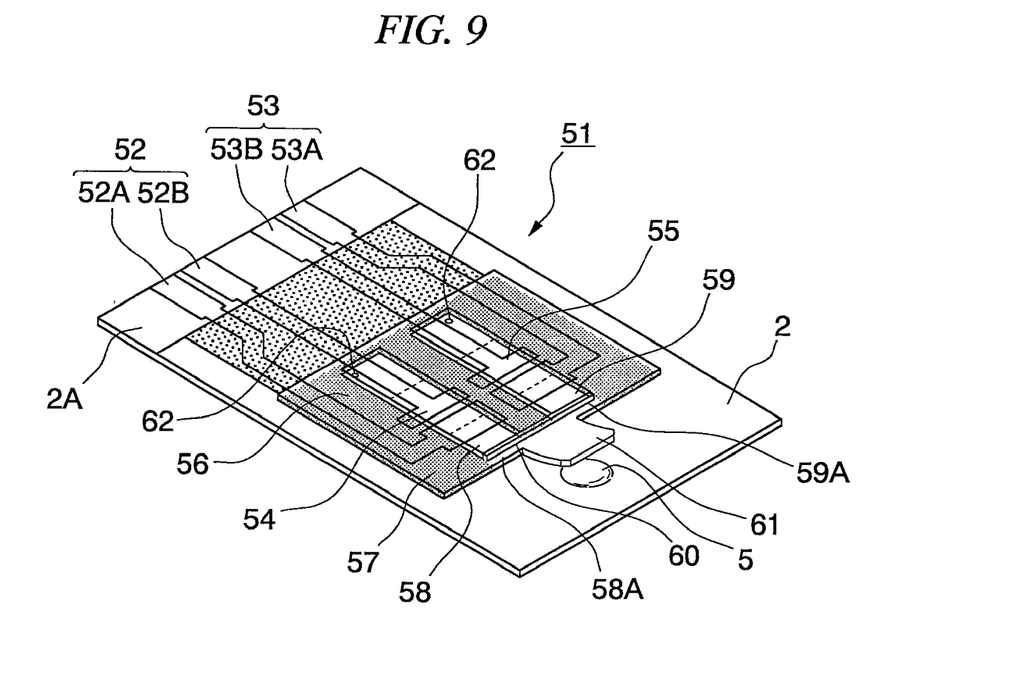
FIG. 9 is a perspective view of the biosensor according to the fourth embodiment of the present invention.

FIG. 9 is a perspective view of the biosensor 51. As shown in FIG. 9, two electrode systems, a first electrode system 52 and a second electrode system 53, are provided to the biosensor 51, and are provided with a design in which measurements are carried out using a conventional differential method.

The first electrode system 52 and the second electrode system 53 are each provided with two electrodes, working electrodes 52A, 53A and counter electrodes 52B, 53B, respectively. A reference electrode is not present in this design. A first test area 54 and a second test area 55 are respectively provided at the ends of the first electrode system 52 and the second electrode system 53 which are opposite the inserted part 2A.

As in the case of the test area 6 in the first embodiment, a first test reagent (test reagent), not shown in the figures, which includes a 1,5-AG oxidoreductase and redox mediator, is disposed to the first test area 54. A second test reagent, not shown in the figures, which includes a redox mediator, but does not include the aforementioned oxidoreductase, is placed to the second test area 55. A cover member 57 is attached via double-sided adhesive tap 56 above the test areas 54, 55. A first sample flow channel 58, which communicates with the first test area 54, and a second sample flow channel 59, which communicates with the second test area 55, are formed according to the shape of the double-sided adhesive tape 56. An air outlet 62 having the same function as the air outlet 15 in the first embodiment is provided to the cover member 57 which is above the test areas 54,55.

A hydrophobic section 60 is provided near the ends (second ends) 58A, 59A of the sample flow channels 58,59 which are opposite the inserted part 2A, so as to transect the sample flow channels 58,59. In addition, an introduced piece 61 is provided so as to bridge each end 58A, 59A. A sample retaining area 5 identical to that of the first embodiment is provided below the introduced piece 61.

The operation of the thus-designed biosensor 51 during use will now be explained.

First, the inserted part 2A of the biosensor 51 is inserted into a detection device (not shown in the figures), and a whole blood sample CS (not shown in the figures) is dripped into the sample retaining area 5 which is below the introduced piece 61. The whole blood sample CS reacts with a pre-treatment reagent, not shown in the figures, to remove the glucose by breakdown, conversion, capture or the like, thereby yielding test sample S.

The pre-treatment reagent employed here may be identical to those cited above. It is acceptable to place this pre-treatment reagent in the sample retaining area 5 or on the upstream side (introduced piece 61 side) of the hydrophobic section 60. In the case where the pre-treatment reagent is placed to the respective sample flow channels 58, 59 on the upstream side of the hydrophobic section 60, the whole blood sample CS is brought into contact with the second hydrophilic section 11 (not shown in the figures) on the back side of the introduced piece 61 by pressing the introduced piece 61. As a result, the whole blood sample CS moves to a position in front of the hydrophobic section 60 and is stopped.

Figure 10:
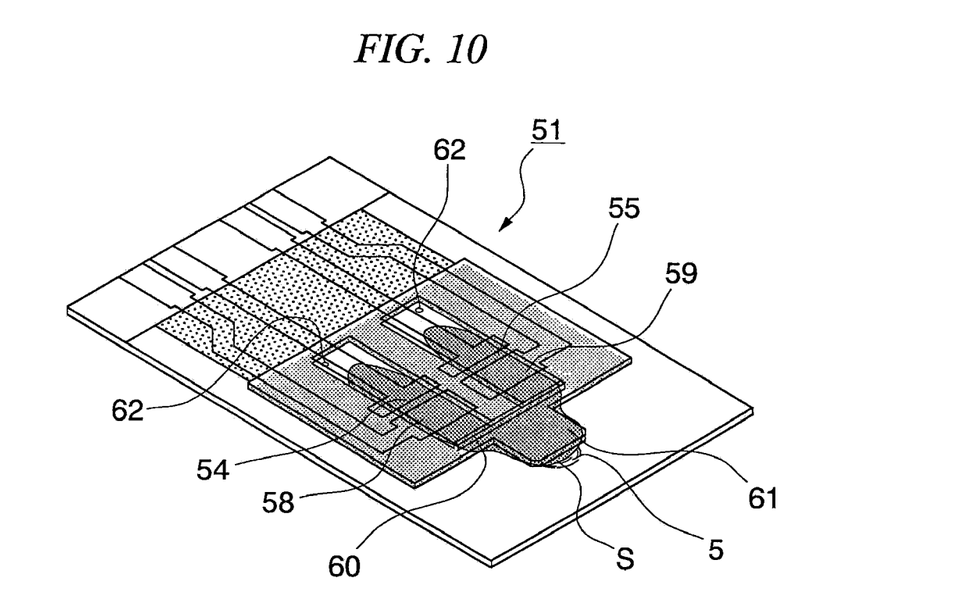
FIG. 10 is a view showing an arrangement in which the sample has been introduced into the biosensor according to the fourth embodiment.
Figure 11:
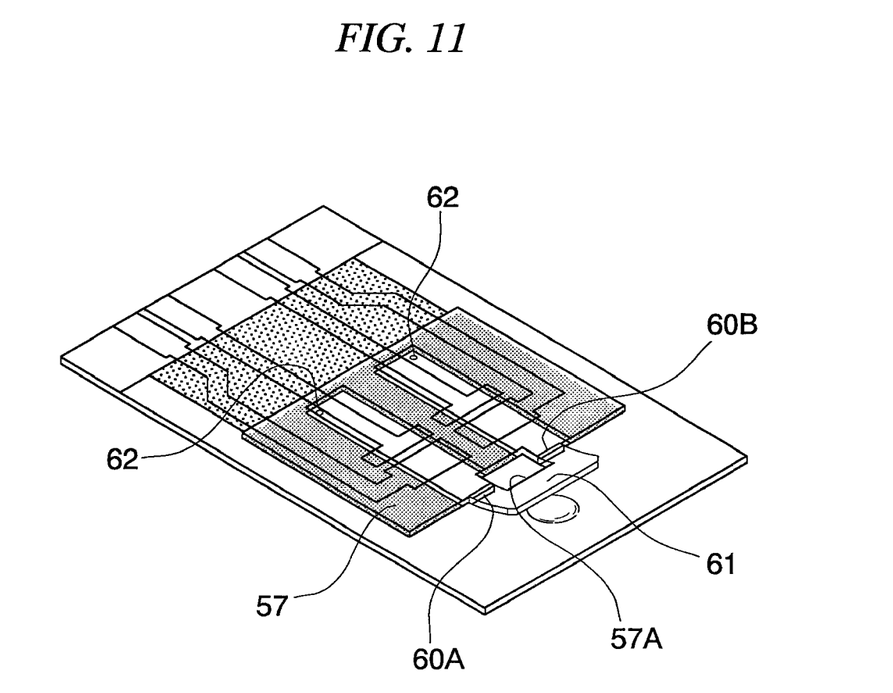
FIG. 11 is a perspective view showing a modification of the biosensor according to the fourth embodiment.

When the user releases the pressure on the hydrophobic section 60, the test sample S surpasses the hydrophobic section 60, flows into the first sample flow channel 58 and the second sample flow channel 59 and moves into the first test area 54 and the second test area 55, respectively, as shown in FIG. 10.

The test sample S which has reached the first test area 54 comes into contact with the first reagent and reacts. The total summed current, which comprises the response current derived from the 1,5-AG in the test sample S and the background current from ascorbic acid, uric acid, etc. in the test sample S, is measured at the first electrode system 52. Conversely, the test sample S which has reached the second test area 55 comes in contact with the second reagent and reacts. Only the aforementioned background current is measured at the second electrode system 53. The detection device measures the concentration of 1,5-AG by subtracting the current value at the second electrode system 53 from the current value at the first electrode system 52, and defining this result as the current value derived from 1,5-AG (differential method).

In the biosensor 51 according to this embodiment, a two electrode system comprising a first electrode system 52 and a second electrode system 53 is provided to the circuit board 2, and sample flow channels 58, 59 corresponding to each of these electrode systems are provided. Accordingly, the 1,5-AG concentration can be measured more accurately using a differential method.

Further, the introduced piece 61 is provided so as to spread to the first sample flow channel 58 and the second sample flow channel 59. Thus, by pushing and then releasing the hydrophobic section 60, the sample can be relayed into both the first sample flow channel 58 and the second sample flow channel 59. Accordingly, a biosensor which is easy to operate can be achieved.

Note that in this embodiment, when the amount of sample is large, it is possible for measurement errors to occur as a result of reagent passing under the introduced piece 61 from one sample flow channel and flowing backward in the other sample flow channel. Accordingly, it is preferable to fix the first and second reagents that are disposed in the respective electrode systems 52, 53 in place using a method employing covalent or other chemical bonding, carriers, etc. By employing this technique, the flow of the respective reagents from the surface of the electrode systems is eliminated. As a result, in the rare circumstance where reverse flow occurs, it does not give rise to measurement errors.

This embodiment explained an example in which the samples in the first sample flow channel 58 and the second sample flow channel 59 area were controlled by means of a hydrophobic section 60 through which they both flow. However, in place of this, as shown by the modification in FIG. 11, it is also acceptable to provide a notch 57A near the area where the introduced piece 61 of the cover member 57 projects out, thereby dividing the hydrophobic section into two parts, 60A and 60B. By providing this design, the sample inside each of the sample flow channels can be controlled by separate hydrophobic sections 60A and 60B, respectively. As a result, it becomes more difficult for the above-described reverse flow to occur. Note that the shape of this notch 57A may be substantially square as shown in FIG. 11, or may be formed to have a substantially pentagonal or triangular shape so that its distal ends narrow on the introduced piece 61 side.

Various embodiments of the present invention were explained above. However, the technical field of the present invention is not limited thereto. Rather, various modifications may be applied as long as they do not depart from the purport of the present invention.

For example, the various embodiments described above explained an example in which the flow stop area was provided at one site only. However, in place of this, it is also acceptable to provide a design in which a plurality of flow stop areas are provided so that the flow of the sample is stopped multiple times before it reaches the electrode system. In this case, a biosensor can be designed in which the different pre-treatment reagents are placed upstream from the various flow stop areas, and the sample is relayed into the electrode system after being stopped at the various flow stop areas where various different pre-treatment reactions are carried out sequentially.

Further, the various embodiments described above explained an example in which the sample flow channel is formed by attaching a cover member onto a circuit board using double-sided adhesive tape. However, in place of this, it is also acceptable to form a sample flow channel by using lasering or the like to form a groove-shaped concave section in the cover member surface which is opposite the circuit board, this groove-shaped concave section serving as the test area and the sample flow channel, and then affixing the concave section to the circuit board by a bonding or heat fusion method. Conversely, it is also acceptable to form a sample flow channel by forming this concave section on the circuit board side.

Further, the various embodiments described above explained an example in which the sample flow channel is open on two ends. However, in place of this, it is also acceptable to design a sample flow channel in which a sample supply port which communicates with the sample flow channel is formed by cutting away a portion of the top surface of the cover member, with the test area and the outside communicating via this sample supply port.

As a result, the sample supply port is open at the top surface of the cover member. Thus, by combining the hydrophilic section and the flow stop area, it is possible to form a biosensor in which the sample can be dripped directly into the sample flow channel and which enables control of the timing at which the sample is moved into the test area of the electrode system.

The various embodiments above explained an example in which a hydrophilic section and a flow stop area are provided to the surface of the cover member that is opposite the circuit board. However, in place of this, it is also acceptable to provide the hydrophilic section and the flow stop area to the circuit board side. In addition, when forming a concave section to the cover member as described above, it is acceptable to provide the hydrophilic section and the flow stop area to the surface of the concave section that is in contact with the circuit board. In addition, the hydrophilic section may be formed by employing the aforementioned hydrophilic film as a spacer. It is not absolutely essential that the hydrophilic section be provided to the entire surface. Rather, the hydrophilic section may be provided as a linear shape which runs in the direction of the flow of the sample.

The decision to form the electrode system from three electrodes, i.e., the working electrode, counter electrode and reference electrode, or from two electrodes, excluding the reference electrode, may be suitably determined based on the properties, etc. of the substance to be measured. For example, when providing one set of electrode systems as in biosensor 1, the electrode system may be formed from two electrodes. When employing a differential method such as in biosensor 51, then the respective electrode systems may be formed of three electrodes.

The preceding embodiments explained an example in which measurements using a differential method were carried out using two pairs of electrode systems. However, in place of this, the reagents required for respective electrical measurements of different substances may be disposed and fixed in place to the various electrode systems. As a result, it is possible to achieve a biosensor that can measure the concentration of two or more substances.

The preceding embodiments explained an example in which the sample was manually moved into the test area. However, in place of this, a design may be provided in which pressure, suction, heat, electromagnetic vibration, voltage or the like is applied from the detection device after the biosensor has been attached thereto, so that the sample automatically moves to the electrode inside the test area. By providing this design, automation of the detection process is further advanced, which is more desirable.

In addition, a sample retaining section and a pre-treatment reagent are not essential design elements in the present invention. Rather, it is acceptable to decide whether or not to dispose the aforementioned, and the details of the disposition, based on the substance to be measured and the sample employed.

For example, when there is only one type of pre-treatment reaction and the amount of required pre-treatment reagent is relatively small, it is acceptable to provide a design in which the flow stop area is provided inside the sample flow channel, the pre-treatment reagent is disposed inside the flow channel, and a sample retaining area is not present. As a result of this design, the pre-treatment reaction is carried out under conditions in which the sample is stopped inside the sample flow channel. Accordingly, this provides an optimal design for automatically moving the sample into the test area by means of a detection device, etc.

On the other hand, by providing a sample retaining area when there are two types of pre-treatment reactions and the amount of required pre-treatment reagent is large, the subsequent steps become easier to carry out.

Further, even in the case where a pre-treatment reaction is not necessary, it can be made easier to carry out the automation of the process employing a detection device or the like, if a flow stop area is provided within the sample flow channel, and the sample is temporarily stopped within the sample flow channel where a pre-treatment reagent is not placed.

What is claimed is:

1. A biosensor for electrochemically measuring a sample, provided with:
    a first member made of an insulating material;
    an electrode system including a working electrode and a counter electrode formed on the first member;
    a second member fixed over the first member so as to cover at least a part of the electrode system;
    a sample flow channel provided between the first member and the second member to allow communication between the outside and a part of the electrode system covered by the second member;
    a first end located at a downstream side end of the sample flow channel;
    a second end located at an upstream side end of the sample flow channel;
    a first hydrophilic section provided on at least a part which is between the first end and the second end contacting with the second end;
    a flow stop area provided on a section adjacent to the second end on the first member or on the internal surface of the sample flow channel between the first end and the second end to temporarily stop the flow of the sample into the electrode system;
    a sample retaining area which is provided to the first member on an upstream side from the second end, and is for retaining the sample which has been dripped down;
    an introduced piece which is provided extending toward the upstream side from the second end side of the sample flow channel of the second member; and
    a second hydrophilic section which is provided on the surface of the introduced piece which faces to the sample retaining area, and which communicates with the first hydrophilic section,
    wherein a part of the electrode system is exposed to an inside of the sample flow channel at a downstream side of the first end,
    wherein the flow stop area is formed of a linear or belt-shaped hydrophobic section which is provided at a downstream side of the sample retaining area so as to stop the sample in a state where it is not contacting the sample flow channel,
    wherein the introduced piece is formed of a material having elasticity, which is capable of moving between a first position at which the introduced piece is bent so as to be distal from the first member, and a second position at which the introduced piece is in proximity of the first member from the first position, and
    wherein the second position is a position at which the sample is introduced into the sample flow channel by a capillary action which occurs between the introduced piece and the first member.

2. A biosensor according to claim 1, wherein said flow stop area is a linear or belt-shaped hydrophobic section which is provided to the internal surface of said sample flow channel so as to transect said first hydrophilic section in the width direction of said sample flow channel.

3. A biosensor according to claim 1, wherein the sample retaining area is formed to have a hydrophilic surface.

4. A biosensor according to claim 1, wherein the sample retaining area is formed to have a step on the first member which is higher than the other area of the first member.

5. A biosensor according to claim 2, wherein said hydrophobic section has a convex section in which the convexity is directed toward said electrode system.

6. A biosensor according to claim 1, wherein the portion of said first member that is opposite said introduced piece is designed to have the same shape as said introduced piece, with said sample flowing up to said flow stop area once said sample is brought into contact with said introduced piece.

7. A biosensor according to claim 1, wherein a plurality of said electrode systems is provided on said first member, with said sample flow channels provided for these respective said electrode systems.

8. A biosensor according to claim 1, wherein said second member is fixed in place to said first member via a spacer which is provided between said first member and said second member, and the side wall of said sample flow channel is formed from said spacer.

9. A biosensor according to claim 1, wherein a pre-treatment reagent is disposed to at least one of either an area of said sample flow channel that is farther toward said second end than said flow stop area, or an area on said first member which is not covered by said second member, said pre-treatment reagent being employed in a pre-treatment reaction on said sample in order to remove, capture or convert to an inert form interfering substances which would hinder said electrochemical measurement.

10. A biosensor according to claim 1, wherein an oxidoreductase and redox mediator is disposed to at least said working electrode in said electrode system.

11. A biosensor according to claim 10, wherein said redox mediator includes at least one of ruthenium derivative, osmium derivative, ferrocyanide derivative, ferrocene derivative, quinone derivative, phenothiazine derivative, phenoxazine derivative, phenazine derivative, indophenol derivative, diphenylamine derivative or phenol derivative.

12. A biosensor according to claim 10, wherein said oxidoreductase includes at least one of pyranose oxidase, L-sorbose oxidase, 1,5-anhydroglucitoldehydrogenase or L-sorbose dehydrogenase.

13. A biosensor according to claim 9, wherein said pre-treatment reagent includes reagent for removing, capturing or converting glucose to another substance which does not effect said electrochemical measurement.

* * * * *